United States Patent [19]

Nutt et al.

[11] Patent Number: 5,057,603
[45] Date of Patent: Oct. 15, 1991

[54] PEPTIDES HAVING ANF ACTIVITY

[75] Inventors: Ruth F. Nutt, Green Lane; Theresa M. Williams, Lansdale; Daniel F. Veber, Ambler; Terry A. Lyle, Lederach, all of Pa.

[73] Assignee: Merck & Co., Inc., Rahway, N.J.

[21] Appl. No.: 571,803

[22] Filed: Aug. 23, 1990

Related U.S. Application Data

[63] Continuation-in-part of Ser. No. 432,358, Sep. 8, 1989, and a continuation of Ser. No. 824,406, Jan. 31, 1986.

[51] Int. Cl.$^5$ .................. A61K 37/02; C07K 7/08; C07K 7/10
[52] U.S. Cl. .................... 530/324; 530/317; 530/325; 530/326
[58] Field of Search .............. 514/13, 12, 11; 530/317, 326, 325, 324

[56] References Cited

U.S. PATENT DOCUMENTS

| | | | |
|---|---|---|---|
| 4,670,540 | 6/1987 | Sakakibara | 530/324 |
| 4,716,147 | 12/1987 | Tjoeng et al. | 514/11 |
| 4,721,704 | 1/1988 | Chang et al. | 514/11 |
| 4,764,504 | 8/1988 | Johnson et al. | 514/12 |
| 4,861,755 | 8/1989 | Breipohl et al. | 514/11 |

FOREIGN PATENT DOCUMENTS

85/04872 11/1985 World Int. Prop. O. ............ 514/11

OTHER PUBLICATIONS

Shiba et al., (Ed.), Pepptide Chemistry 1987, pp. 502–506, Protein Research Foundation, Osaka, 1987.
Rivier et al., (Ed.) Peptides: Chemistry, Structure and Biology, 1990, pp. 258–259, ESCOM, Leiden, 1990.

*Primary Examiner*—Howard E. Schain
*Assistant Examiner*—Susan M. Perkins
*Attorney, Agent, or Firm*—Frank P. Grassler; Donald J. Perrella; Hesna J. Pfeiffer

[57] ABSTRACT

Novel peptides having potent natriuretic activity are disclosed with the following amino acid sequence:

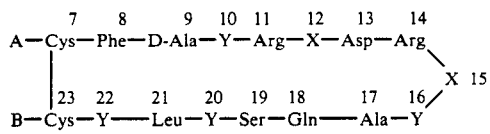

wherein X is L-Ile, D-Ile, D-allo-Ile, L-Met or D-Met, Y is Gly, L-Ala or D-Ala, A is optionally absent or is Ser, Ser-Ser, Arg-Ser-Ser, Arg-Arg-Ser-Ser, Leu-Arg-Arg-Ser-Ser or Ser-Leu-Arg-Arg-Ser-Ser and B is optionally absent or is Asn, Asn-Ser, Asn-Ser-Phe, Asn-Ser-Phe-Arg, or Asn-Ser-Phe-Arg-Tyr, provided that at least one of $Y^{10}$, $Y^{16}$, $Y^{20}$ or $Y^{22}$ is Ala or D-Ala, and the amides, lower alkyl esters and the physiologically acceptable metal salts and acid addition salts thereof.

16 Claims, No Drawings

PEPTIDES HAVING ANF ACTIVITY

RELATED APPLICATION

This is a continuation-in-part of copending application Ser. No. 432,358 filed Sept. 8, 1989 as a continuation of copending application 824,406 filed Jan. 31, 1986.

BACKGROUND OF THE INVENTION

It has been postulated for many years that the cardiac atria serve as sensors that are important in detecting changes in extracellular fluid volume (Gauer et al., Physiol. Rev. 43: 423, 1963). Such a receptor function for the cardiac atria is known in the case of vasopressin, the hypothalmic hormone important in regulating the osmotic concentration of the body fluids.

The postulated existence of a substance which would enhance urinary sodium excretion, and hence be involved in regulation of extracellular fluid volume, was demonstrated recently. de Bold et al., Life Sci. 28: 89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221: 71, 1983). Such action implies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor or ANF but has been referred to also as cardionatrin (de Bold et al., Life Sci. 33: 297-302, 1983) and atriopeptin (Currie et al., Science 111: 67, 1984).

DESCRIPTION OF EARLIER ARTICLES AND PATENTS

Thibault et al., FEBS Lett. 164 (2): 286-290 (1983), discloses three peptides of 26, 31 and 33 amino acids and gives their amino acid composition but does not give any amino acid sequences. Since these peptides were isolated from rat atria, all optically active amino acids have L-configuration.

Flynn et al., Biochem. Biophys. Res. Comm. 117 (3): 859-865 (1983), discloses a 28-amino acid

```
 6    7    8    9   10   11
Ser—Leu—Arg—Arg—Ser—Ser—

12   13   14   15   16   17   18   19   20   21
Cys—Phe—Gly—Gly—Arg—Ile—Asp—Arg—Ile—Gly—
 |
 |
22   23   24   25   26   27  | 28   29   30   31
Ala—Gln—Ser—Gly—Leu—Gly—|Cys—Asn—Ser—Phe—
```

-continued

```
32   33
Arg—Tyr.
```

Since this peptide was isolated from rat atria, all optically active amino acids have L-configuration.

Currie et al., Science 223: 67-69 (1984), disclose two peptides having sequences 10-30 and 1-32 (numbering as above). Since these peptides were isolated from rat atria, all optically active amino acids have L-configuration.

Kangawa et al., Biochem. Biophys. Res. Comm. 118 (1): 131-139 (1984), disclose a 28-amino acid peptide having sequence 6-33 (numbering as above) having a methionine residue in lieu of isoleucine in 17-position. Since this peptide was isolated from atrial tissue, all optically active amino acids have L-configuration.

Thibault et al., FEBS Lett. 167 (2): 352-357 (1984), disclose isolation of a peptide of 103 amino acids and give the sequence of the C-terminal 73-amino acid fragment. The three peptides disclosed by Thibault et al., supra, correspond to C-terminal fragments of this peptide. Since all of these peptides were isolated from rat atria, and one that was synthesized conformed to the shortest one isolated, all optically active amino acids have L-configuration.

Misono et al., Biochem. Biophys. Res. Comm. 119 (2): 524-529 (1984), disclose isolation of a 25-amino acid peptide of sequence 9-33 (numbering as above). Since this peptide was isolated from rat atria, all optically active amino acids have L-configuration.

Needleman et al., U.S. Pat. No. 4,496,544, discloses isolation from several peptides of sequences 12-29, 12-30, 12-32, 12-33, 11-29, 11-30, 11-32, 11-33, 10-29, 10-30, 10-32 and 10-33 (numbering as above). Since all of these peptides were isolated from rat atria, all optically active amino acids have L-configuration.

European patent specification 0 369 474 discloses compositions containing ANF peptides that are useful for the treatment of cerebral edema.

OBJECTS OF THE INVENTION

It is an object of the present invention to provide novel peptides having activity like that of ANF peptides isolated from biological materials. Another object is to provide novel peptides having potent natriuretic, vasodilatory and hypotensive activity. A further object is to provide novel peptides having enhanced metabolic stability. These and other objects of the present invention will be apparent from the following description.

SUMMARY OF THE INVENTION

Novel peptides having potent natriuretic activity are disclosed with the following amino acid sequence:

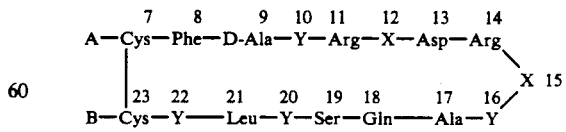

wherein X is L-Ile, D-Ile, D-allo-Ile, L-Met or D-Met, Y is Gly, L-Ala or D-Ala, optionally absent or is H, Ser, Ser-Ser, Arg-Ser-Ser, Arg-Arg-Ser-Ser, Leu-Arg-Arg-Ser-Ser or Ser-Leu-Arg-Arg-Ser-Ser and B is optionally absent or is Asn, Asn-Ser, Asn-Ser-Phe, Asn-Ser-Phe-Arg, or Asn-Ser-Phe-Arg-Tyr, provided that at least one of $Y^{10}$, $Y^{16}$, $Y^{20}$ or $Y^{22}$ is Ala or D-Ala, and the amides, lower alkyl esters and the physiologically acceptable metal salts and acid addition salts thereof.

DETAILED DESCRIPTION

It has now been found that novel peptides having activity like that of ANF peptides isolated from biological materials, e.g., potent natriuretic, vasodilatory and hypotensive activity, but with enhanced metabolic stability are obtained by substituting at least one D-amino acid for its L counterpart, or by substituting at least one L-alanine or D-alanine for glycine.

The novel peptides of the present invention are as follows:

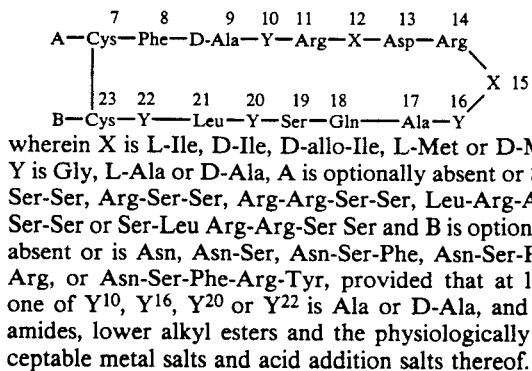

wherein X is L-Ile, D-Ile, D-allo-Ile, L-Met or D-Met, Y is Gly, L-Ala or D-Ala, A is optionally absent or Ser, Ser-Ser, Arg-Ser-Ser, Arg-Arg-Ser-Ser, Leu-Arg-Arg-Ser-Ser or Ser-Leu Arg-Arg-Ser Ser and B is optionally absent or is Asn, Asn-Ser, Asn-Ser-Phe, Asn-Ser-Phe-Arg, or Asn-Ser-Phe-Arg-Tyr, provided that at least one of $Y^{10}$, $Y^{16}$, $Y^{20}$ or $Y^{22}$ is Ala or D-Ala, and the amides, lower alkyl esters and the physiologically acceptable metal salts and acid addition salts thereof.

D-Amino acids introduce a residue at which normal proteolytic enzymes no longer can act. They also modify and rigidify conformation at adjacent amino acids. This is particularly true when glycine is replaced by D-alanine. Decreased conformational flexibility is known to reduce peptide susceptibility to enzyme cleavage. Thus, replacing glycine with L-alanine enhances metabolic stability even though the residue itself is the natural substrate of many proteolytic enzymes. The enhanced potency of some of these analogs probably reflects the decreased flexibility.

The ANF peptides of the present invention may be prepared from their constituent amino acids by standard methods of protein synthesis, e.g., Schroeder et al., "The Peptides", Vol. I, Academic Press, 1965, or Bodanszky et al., "Peptide Synthesis", Interscience Publishers 1966, or McOmie (ed.), "Protective Groups in Organic Chemistry", Plenum Press 1973, and "The Peptides: Analysis, Synthesis, Biology" 2, Chapter 1 by George Barany and R. B. Merrifield, Academic Press, 1980, New York.

The peptides of the invention may be prepared using solid phase synthesis, such as that described by Merrifield, J. Am. Chem. Soc.. 85, 2149 (1964) or other equivalent chemical syntheses known n the art such as the syntheses of Houghten, Proc. Natl. Acal. Sci.. 82. 5132 (1985). Paying particular attention to treatment of the protein containing solution following HF cleavage. Solid phase synthesis is commenced from the C-terminus of the peptide by coupling a protected amino acid to a suitable resin, as generally set forth in U.S. Pat. No. 4,244,946, the disclosure of which is hereby incorporated by reference. Other examples of synthesis of this general type are set forth in U.S. Pat. Nos. 4,305,872 and 4,316,891.

In synthesizing the polypeptides, the carboxyl terminal amino acid, having its alpha-amino group suitable protected, is coupled to a chloromethylated polystyrene resin or the like. After removal of the alpha-amino protecting group, as by using trifluoroacetic acid in methylene chloride, the next step in the synthesis is ready to proceed. Other standard cleaving reagents and conditions for the removal of specific amino protecting groups may be used, as described in published literature.

The remaining alpha-amino- and side chain-protected amino acids are then coupled stepwise in the desired order by condensation to obtain an intermediate compound connected to the resin. As an alternative to adding each amino acid separately in the synthesis some of them may be coupled to one another prior to the addition to the growing solid-phase chain. The selection of the appropriate coupling reagents is within the skill of the art.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method, etc), or Woodward reagent K method. In the case of elongating the peptide chain in the solid phase method, the peptide is attached to an insoluble carrier at the C terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, p-hydroxymethylphenylacetamide (PAM) resin, benzhydrylamine resin, and t-alkyloxycarbonyl-hydrazide resin can be used.

Common to chemical syntheses of peptides is the protection of the reactive side-chain groups of the various amino acid moieties with suitable protecting groups at that site until the group is ultimately removed after the chain has been completely assembled. Also common is the protection of the alpha-amino group on an amino acid or a fragment while that entity reacts at the carboxyl group followed by the selective removal of the alpha-amino-protecting group to allow subsequent reaction to take place at that location. Accordingly, it is common that as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for Protecting the alpha- and omega-side chain amino groups are, for example, benzyloxycarbonyl (hereinafter abbreviated as Z), isonicotinyl oxycarbonyl (iNOC), o-chlorobenzyloxycarbonyl [Z(2Cl)], p-nitrobenzyloxycarbonyl [Z(NO₂)], p-methoxybenzyloxycarbonyl [Z(OMe)], t-butoxycarbonyl, (Boc), t-amyloxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonyl ethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for the carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1, 3, 5-trimethylphenysulfonyl (Mts), and the like. The thiol group in cysteine may be protected with p-methoxybenzyl, triphenylmethyl, acetylaminomethyl, ethylcarbamoyle, 4-methylbenzyl, 2, 4, 6-trimethybenzyl (Tmb) etc, and the hydroxyl group in serine can be protected with benzyl, t-butyl, acetyl, tetrahydropyranyl etc.

Stewart and Young, "Solid Phase Peptide Synthesis", Pierce Chemical Company, Rockford, Ill. (1984) provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151. These descriptions are hereby incorporated by reference.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side chain protecting groups.

Preferably, in order to avoid alkylation of residues in the polypeptide (for example, alkylation of methionine, cysteine, and tyrosine residues), a thio-cresol and cresol scavenger mixture is used. The resin is washed with ether, and immediately transferred to a large volume of dilute acetic acid to solubilize and minimize intermolecular cross-linking. A 250 μM polypeptide concentration is diluted in about 2 liters of 0.1M acetic acid solution. The solution is then stirred and its pH adjusted to about 8.0 using ammonium hydroxide. Upon pH adjustment and exposure to air, the polypeptide takes its desired conformational arrangement. Conversion of the linear peptides to the cyclic disulfides may also be carried out using $I_2$ in 20–50% aqueous acetic acid or DMF.

The ANF peptides of the present invention also may be prepared using manufacturer supplied protocols with automated peptide synthesizing machines, e.g. Beckman, Applied Biosystems Inc., or Milligen Co.

One therapeutic utility of the ANF peptides of the present invention is to relax vascular muscle in various disease states where standard therapy utilizes potent diuretics in combination with peripheral vasodilating drugs. Atrial natriuretic factor combines both of these actions in one molecule which is produced naturally within the body.

In addition, a second major therapeutic utility of the ANF peptides of the present invention is in essential hypertension. Standard therapy for hypertension utilizes diuretic and peripheral vasodilating drugs. Atrial natriuretic factor incorporates both of these characteristics. A specific use also may be found in the acute treatment of hypertensive crisis such as malignant hypertension where the powerful vasodilating effect of ANF is desired.

Another therapeutic utility of the peptides of the present invention is in disorders of altered vascular resistance arising as a secondary effect following heart failure or renal failure.

The peptides of the present invention are useful individually or in combination to treat disorders of electrolyte balance and/or altered vascular resistance in a mammalian species, e.g., mice and rats, in amount of from about 10 picomoles/kg/min. to about 300 nanomoles/kg/min., preferably from about 100 to about 1000 picomoles/kg/min. The peptides may be administered by intravenous infusion, for example in a suitable physiologically acceptable carrier, e.g., saline or phosphate buffered saline.

The peptides of this invention or their amides, or lower alkyl esters or metal salts or acid addition salts with pharmaceutically acceptable acids are administered to a mammalian species, e.g., rats or mice, systemically, either by intravenous, subcutaneous, or intramuscular injection, or by sublingual or nasal administration, in compositions in conjunction with pharmaceutically acceptable vehicles or carriers. For administration by injection or by the nasal route it is preferred to use the peptides in solution in a sterile aqueous vehicle which may also contain other solutes such as buffers or preservatives as well as sufficient quantities of pharmaceutically acceptable salts or of glucose to make the solution isotonic. In addition, when the above compositions are intended for use as sprays for nasal administration they may also contain small amounts of a pharmaceutically acceptable surface active agent to ensure rapid absorption of the respective peptide by the nasal mucosa. Examples of such surface-active agents are polysorbate 80 (Tween 80), benzalkonium chloride, bile salts such as sodium glycocholate, dioctyl sodium sulfosuccinate (Aerosol OT), and the like. For sublingual administration it is preferred to formulate the peptides of this invention as rapidly dissolving tablets together with solid excipients or carriers such as lactose. Examples of such excipients or carriers are found in standard pharmaceutical texts, e.g., in Remington's Pharmaceutical Sciences, Mack Publishing Company, Easton, Pa., 1970. Intranasal or sublingual administration may be less precise than intravenous injection but it may be a more convenient form of treatment.

When administration of the peptides of the present invention is desired for the obtention of diuretic, natriuretic, vasorelaxant, hypotensive, or antihypertensive effects such as e.g., in the treatment of hypertension, in particular renovascular hypertension, or in treatment of cerebral edema the dosage to be administered will depend upon such factors as the species, age, weight, sex, and condition of the patient and with the chosen form of administration. Generally, treatment is initiated with small dosages substantially less than the optimum dose of the respective peptide. Thereafter, the dosage is increased by small increments until the optimal effect under the given circumstances is reached. In general, the peptides of this invention are most desirably administered at dosage levels which will give effective concentrations of the respective peptide in the blood of the patient without causing any harmful or deleterious side effects, and preferably at a level that is in the range of from about 0.02 mcg to about 200 mcg per kilogram body weight, although as aforementioned variations will occur. However, for infusion a dosage level that is in the range of from about 0.1 mcg to about 1000 mcg/minute/kg is most desirably employed to achieve effective results. Single doses may be administered in a dosage level of from about 0.01 to about 10 mg in one or more divided doses.

It is often desirable to administer the Peptides of this invention continuously over prolonged periods of time in long acting, slow-release, or depot dosage forms. Such dosage forms may either contain a pharmaceutically acceptable salt of the respective peptide having a low degree of solubility in body fluids, for example one of those salts described above, or they may contain the peptide in the form of a water-soluble salt together with a protective carrier which prevents rapid release. In the latter case, for example, the peptide may be formulated with a non-antigenic partially hydrolyzed gelatin in the form of a viscous liquid; or the peptide may be absorbed on a pharmaceutically acceptable solid carrier, for example zinc hydroxide, and may be administered in suspension in a pharmaceutically acceptable liquid vehicle; or the peptide may be formulated in gels or suspensions with a protective non-antigenic hydrocolloid, for example sodium carboxymethylcellulose, polyvinylpyrrolidone, sodium alginate, gelatin, polygalacturonic acids, for example, pectin, or certain mucopolysaccharides, together with aqueous or nonaqueous pharmaceutically acceptable liquid vehicles, preservatives, or surfactants. Examples of such formulations are found in standard pharmaceutical texts, e.g., in Remington's Pharmaceutical Sciences cited above. Long-acting, slow-release preparations of the peptides of this invention may also be obtained by microencapsulation in a pharmaceutically acceptable coating material, for example gelatin, polyvinyl alcohol or ethyl cellulose. Further examples of coating materials and the processes used for microencapsulation are described by J. A. Herbig in Encyclopedia of Chemical Technology, Vol. 13, 2nd Ed., Wiley, New York 1967, pp. 436–456. Such formulations, as well as suspensions of salts of the peptide which are only sparingly soluble in body fluids, are designed to release from about 0.02 mcg to about 20 mcg of the peptide per kilogram body weight per day, and are preferably administered by intramuscular injection. Alternatively, some of the solid dosage forms listed above, for example certain sparingly water soluble salts or dispersions in or adsorbates on solid carriers of salts of the peptides, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

In the following examples, standard single letter abbreviations for amino acid residues are employed:

| | |
|---|---|
| Alanine | A |
| D-Alanine | D-A |
| Glycine | G |
| Isoleucine | I |
| Methionine | M |

In accordance with the present disclosure, peptides of the present invention include the following:

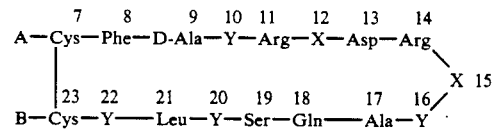

wherein A is Arg Ser Ser, B is Asp Ser Phe Arg Tyr, and $Y^{10}$, $X^{12}$, $X^{15}$, $Y^{16}$, $Y^{20}$ and $Y^{22}$ are the following amino acid residues:

| | $Y^{10}$ | $X^{12}$ | $X^{15}$ | $Y^{16}$ | $Y^{20}$ | $Y^{22}$ |
|---|---|---|---|---|---|---|
| 1 | A | I | I | A | A | D-A |
| 2 | G | I | I | A | A | G |
| 3 | A | I | I | G | G | G |
| 4 | G | I | I | A | G | G |
| 5 | A | I | I | G | G | G |
| 6 | A | I | I | G | G | D-A |
| 7 | G | M | I | A | G | G |
| 8 | G | M | I | D-A | G | G |
| 9 | G | I | M | G | A | G |
| 10 | G | M | M | G | D-A | G |
| 11 | G | I | I | G | G | A |
| 12 | G | I | I | G | G | A |
| 13 | A | I | I | A | G | G |
| 14 | A | I | I | D-A | G | G |
| 15 | G | I | I | A | A | G |
| 16 | A | I | I | A | A | G |
| 17 | A | I | I | A | A | D-A |

Other peptides of the present invention include peptide of the foregoing general formula wherein residues 10 and 22 are Gly, residues 16 and 20 are Ala except for the final peptide where residue 16 is Ala and 20 is Gly, and A and B are the residues indicated below.

| | A | B | C-Terminus |
|---|---|---|---|
| 18 | Arg Ser Ser | Asp Ser Phe Arg Tyr | COOH |
| 19 | Ser Ser | Asp Ser Phe Arg Tyr | COOH |
| 20 | Ser | Asp Ser Phe Arg Tyr | COOH |
| 21 | Arg Arg Ser Ser | Asp Ser Phe Arg | COOH |
| 22 | Arg Ser Ser | Asp Ser Phe Arg | COOH |
| 23 | Ser Ser | Asp Ser Phe Arg | COOH |
| 24 | Ser | Asp Ser Phe Arg | COOH |
| 25 | — | Asp Ser Phe Arg | $CONH_2$ |

The following examples illustrate the present invention without, however, limiting the same thereto.

EXAMPLE 1

The following peptides of the present invention (the numbers refer to the correspondingly numbered peptides in the section immediately preceding this example), were prepared by solid phase method using an ABI 430A automated synthesizer and removed from the resin with HF. When Cys was protected with p-methyl benzyl, all protecting groups were removed by the action of HF. Cyclization was then accomplishd by air oxidation in dilute aqueous medium at neutral to basic pH of by $I_2$ in aqueous acetic acid. When Cys was protected with Acm, treatment with HF removed all protecting groups except Acm which was then removed by the action of $I_2$ with concommtant cyclization. In peptides 1-4, the substituent A was Arg Arg Ser Ser and the substituent B was Asp Ser Phe Arg Tyr, while in peptide 25, A was not present and B was Asp Ser Phe Arg.

| Peptide | Residues | 10 | 16 | 20 | 22 | C-terminus |
|---|---|---|---|---|---|---|
| 1 | 3-28 | Ala | Ala | Ala | D-Ala | COOH |
| 2 | 3-28 | Gly | Ala | Ala | Gly | COOH |
| 3 | 3-28 | Ala | Gly | Gly | Gly | COOH |
| 4 | 3-28 | Gly | Ala | Gly | Gly | COOH |
| 25 | 7-27 | Gly | Ala | Gly | Gly | $CONH_2$ |

EXAMPLE 2

The following table shows the potencies of representative peptides of the present invention in relaxing rabbit aorta compared to the corresponding non-substituted 3-28 or 7-27 amide reference analogs when tested essentially by the method of Winquist et al., European Journal of Pharmacology 102: 169–173 (1984).

| Peptide of Example 1 | Relative Potency |
|---|---|
| 1 | 1.38 |
| 2 | 23. |
| 3 | 2.9 |
| 4 | 3.76 |
| 25 | 4.8 |

What is claimed is:

1. A peptide of the amino acid sequence:

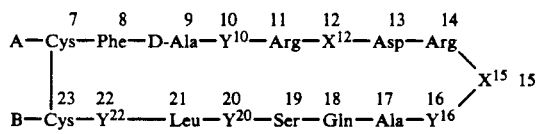

wherein
A is absent or is
 Ser,
 Ser-Ser,
 Arg-Ser-Ser,
 Arg-Arg-Ser-Ser,
 Leu-Arg-Arg-Ser-Ser, or
 Ser-Leu-Arg-Arg-Ser-Ser;
B is absent or is
 Asn,
 Asn-Ser,
 Asn-Ser-Phe,
 Asn-Ser-Phe-Arg, or
 Asn-Ser-Phe-Arg-Tyr;
and $Y^{10}$, $X^{12}$, $X^{15}$, $Y^{16}$, $Y^{20}$ and $Y^{22}$ are selected from one of the amino acid sets comprising

| $Y^{10}$ | $X^{12}$ | $X^{15}$ | $Y^{16}$ | $Y^{20}$ | $Y^{22}$ |
|---|---|---|---|---|---|
| Ala | Ile | Ile | Ala | Ala | D-Ala, |
| Gly | Ile | Ile | Ala | Ala | Gly, |
| Ala | Ile | Ile | Gly | Gly | Gly, |
| Gly | Ile | Ile | Ala | Gly | Gly, |
| Ala | Ile | Ile | Gly | Gly | D-Ala, |
| Gly | Met | Ile | Ala | Gly | Gly, |
| Gly | Ile | Ile | Gly | Gly | Ala, |
| Ala | Ile | Ile | Ala | Gly | Gly, |
| Ala | Ile | Ile | D-Ala | Gly | Gly and |
| Ala | Ile | Ile | Ala | Ala | Gly. |

2. A peptide as claimed in claim 1, wherein the amino acid set corresponding to $Y^{10}$, $X^{12}$, $X^{15}$, $Y^{16}$, $Y^{20}$ and $Y^{22}$ is Ala Ile Ile Ala Ala D-Ala.

3. A peptide as claimed in claim 1, wherein the amino acid set corresponding to $Y^{10}$, $X^{12}$, $X^{15}$, $Y^{16}$, $Y^{20}$ and $Y^{22}$ is Gly Ile Ile Ala Ala Gly.

4. A peptide as claimed in claim 1, wherein the amino acid set corresponding to $Y^{10}$, $X^{12}$, $X^{15}$, $Y^{16}$, $Y^{20}$ and $Y^{22}$ is Ala Ile Ile Gly Gly Gly.

5. A peptide as claimed in claim 1, wherein the amino acid set corresponding to $Y^{10}$, $X^{12}$, $X^{15}$, $Y^{16}$, $Y^{20}$ and $Y^{22}$ is Gly Ile Ile Ala Gly Gly.

6. A peptide as claimed in claim 1, wherein the amino acid set corresponding to $Y^{10}$, $X^{12}$, $X^{15}$, $Y^{16}$, $Y^{20}$ and $Y^{22}$ is Ala Ile Ile Gly Gly D-Ala.

7. A peptide as claimed in claim 1, wherein the amino acid set corresponding to $Y^{10}$, $X^{12}$, $X^{15}$, $Y^{16}$, $Y^{20}$ and $Y^{22}$ is Gly Met Ile Ala Gly Gly.

8. A peptide as claimed in claim 1, wherein the amino acid set corresponding to $Y^{10}$, $X^{12}$, $X^{15}$, $Y^{16}$, $Y^{20}$ and Y22 is Gly Ile Ile Gly Gly Ala.

9. A peptide as claimed in claim 1, wherein the amino acid set corresponding to $Y^{10}$, $X^{12}$, $X^{15}$, $Y^{16}$, $Y^{20}$ and $Y^{22}$ is Ala Ile Ile Ala Gly Gly.

10. A peptide as claimed in claim 1, wherein the amino acid set corresponding to $Y^{10}$, $X^{12}$, $X^{15}$, $Y^{16}$, $Y^{20}$ and $Y^{22}$ is Ala Ile Ile D-Ala Gly Gly.

11. A peptide as claimed in claim 1, wherein the amino acid set corresponding to $Y^{10}$, $X^{12}$, $X^{15}$, $Y^{16}$, $Y^{20}$ and $Y^{22}$ is Ala Ile Ile Ala Ala Gly.

12. A peptide according to claim 1 in combination with a pharmaceutically acceptable carrier.

13. A method of treating a disorder of electrolyte balance which comprises administering to a mammalian species an amount of a peptide of claim 1, that is effective to ameliorate the electrolyte balance.

14. A method of lowering hypertension which comprises administering to a mammalian species an amount of a peptide of claim 1, that is effective to lower hypertension.

15. A pharmaceutical composition comprising an effective amount of a compound of claim 1 and a pharmacologically acceptable carrier.

16. A composition of claim 15 wherein the amount of the compound is from about 0.02 mcg to about 20 mcg.

* * * * *